US008945145B2

(12) United States Patent  
Tran et al.

(10) Patent No.: US 8,945,145 B2  
(45) Date of Patent: Feb. 3, 2015

(54) DELIVERY SYSTEM ASSEMBLIES FOR IMPLANTABLE MEDICAL DEVICES

(75) Inventors: Don H. Tran, Novato, CA (US); William A. Berthiaume, Santa Rosa, CA (US); H. Allan Steingisser, Windsor, CA (US); Maria Valdovinos, Santa Rosa, CA (US); Brent L. Locsin, San Francisco, CA (US); Suruchi Anand, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 639 days.

(21) Appl. No.: 13/239,990

(22) Filed: Sep. 22, 2011

(65) Prior Publication Data

US 2013/0079798 A1    Mar. 28, 2013

(51) Int. Cl.
| | |
|---|---|
| *A61B 19/00* | (2006.01) |
| *A61B 17/34* | (2006.01) |
| *A61N 1/372* | (2006.01) |
| *A61N 1/375* | (2006.01) |
| *A61N 1/362* | (2006.01) |

(52) U.S. Cl.
CPC ........ *A61B 17/3468* (2013.01); *A61N 1/37205* (2013.01); *A61N 1/3756* (2013.01); *A61N 1/362* (2013.01)
USPC .......................................... 606/129; 623/1.11

(58) Field of Classification Search
CPC ........... A61F 2/95; A61F 2/962; A61F 2/966; A61F 2/97; A61F 2002/95; A61F 2002/9505; A61F 2002/9517; A61F 2002/9534; A61F 2002/962; A61F 2002/966; A61F 2002/9665
USPC .................................. 623/1.11, 1.12; 606/129
See application file for complete search history.

(56) References Cited

U.S. PATENT DOCUMENTS

| | | |
|---|---|---|
| 3,943,936 A | 3/1976 | Rasor et al. |
| RE30,366 E | 8/1980 | Rasor et al. |
| 5,334,160 A | 8/1994 | Ellis |
| 6,074,379 A | 6/2000 | Prichard |
| 6,102,890 A | 8/2000 | Stivland et al. |
| 7,369,901 B1 | 5/2008 | Morgan et al. |
| 7,444,180 B2 | 10/2008 | Kuzma et al. |

(Continued)

FOREIGN PATENT DOCUMENTS

WO    2006/099425    9/2006

OTHER PUBLICATIONS (PCT/US2012/056029) PCT Notification of Transmittal of the International Search Report and the Written Opinion of the International Searching Authority.

*Primary Examiner* — Thomas McEvoy

(74) *Attorney, Agent, or Firm* — Evans M. Mburu

(57) ABSTRACT

A delivery system assembly includes an elongate inner member that extends distally through a lumen of an elongate outer tube of the assembly; the outer tube is moveable relative to the inner member between first and second positions to deploy an implantable medical device that is held within the outer tube lumen. The inner member may include a flared distal end that abuts, and preferably conforms to, the proximal end of the device, when the device is held within the outer tube lumen. The assembly further includes a stability sheath that surrounds a limited length of the outer tube, in proximity to the handle, to provide an interface for both an operator, who handles the assembly, and for an introducer sheath that provides passage for the assembly into the venous system, so that movement of the outer tube is not hindered by either during device deployment.

13 Claims, 6 Drawing Sheets

(56) References Cited

U.S. PATENT DOCUMENTS

| | | | |
|---|---|---|---|
| 2004/0210211 A1* | 10/2004 | Devens et al. | 604/523 |
| 2005/0090890 A1 | 4/2005 | Wu et al. | |
| 2006/0241732 A1 | 10/2006 | Denker et al. | |
| 2007/0088418 A1 | 4/2007 | Jacobson | |
| 2007/0150037 A1 | 6/2007 | Hastings et al. | |
| 2007/0250150 A1* | 10/2007 | Pal et al. | 623/1.11 |
| 2007/0270932 A1 | 11/2007 | Headley et al. | |
| 2008/0039904 A1 | 2/2008 | Bulkes et al. | |
| 2010/0274187 A1* | 10/2010 | Argentine | 604/96.01 |
| 2011/0139754 A1 | 6/2011 | Romanowski et al. | |

* cited by examiner

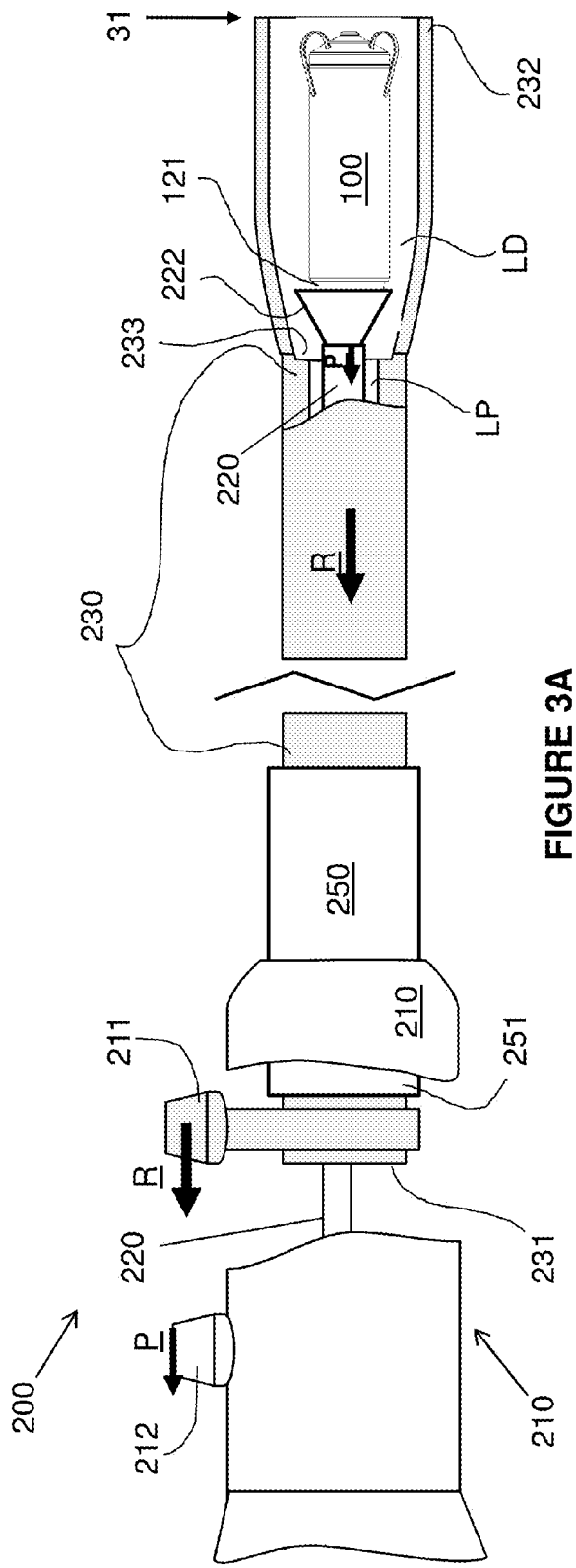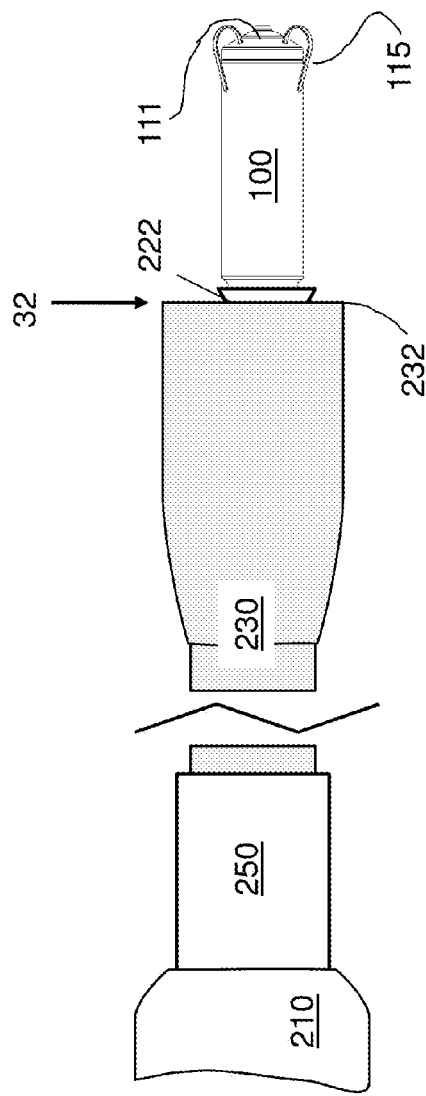
FIGURE 3A
FIGURE 3B

DELIVERY SYSTEM ASSEMBLIES FOR IMPLANTABLE MEDICAL DEVICES

TECHNICAL FIELD

The present invention pertains to delivery system assemblies for implantable medical devices, and more particularly to delivery system assemblies configured to facilitate percutaneous transvenous deployment of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing devices that are wholly contained within a relatively compact package for implant in close proximity to the pacing site, for example, within the right ventricle (RV) of the heart. With reference to FIG. 1A, such a device 100 is illustrated, wherein pace/sense electrodes 111, 112 are formed on an exterior surface of an enclosure 101 that hermetically contains a pulse generator including pulse generator electronics and a power source. FIG. 1A further illustrates a fixation member 115 mounted to an end of enclosure 101, in proximity to electrode 111, in order to fix, or secure electrode 111 against the endocardial surface in the apex of the RV. Enclosure 101 is preferably formed from a biocompatible and biostable metal such as titanium overlaid with an insulative layer, for example, medical grade polyurethane or silicone, except where electrode 112 is formed as an exposed portion of capsule 101. A hermetic feedthrough assembly (not shown), such as any known to those skilled in the art, couples electrode 111 to the pulse generator contained within enclosure 101.

FIG. 1B illustrates a distal portion of a standard guiding catheter 150 having been maneuvered up through the inferior vena cava IVC and into the RV from the right atrium (RA), according to methods known in the art of interventional cardiology. Although device 100 may be delivered to the RV, for implant, through catheter 150, improved delivery means are desirable to deploy device 100 at the implant site.

SUMMARY

A delivery system assembly, according to embodiments of the present invention includes an elongate inner member that extends distally through a lumen of an elongate outer tube of the assembly; the outer tube is retractable relative to the inner member, from a first position to a second position, in order to deploy an implantable medical device that is held within the outer tube lumen in proximity to a distal end thereof. The inner member may include a flared distal end that abuts, and preferably conforms to, the proximal end of the device, when the device is held within the outer tube lumen. The assembly further includes a stability sheath that surrounds a limited length of the outer tube, in proximity to the handle, to provide an interface for both an operator, who handles the assembly, and for an introducer sheath, which may provide passage for the assembly into the venous system, so that retraction of the outer tube is not hindered by either during device deployment.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIG. 3A is an enlarged plan view, including cut-away sections, of distal and proximal portions of the delivery system assembly;

FIG. 3B is another plan view of the system assembly;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
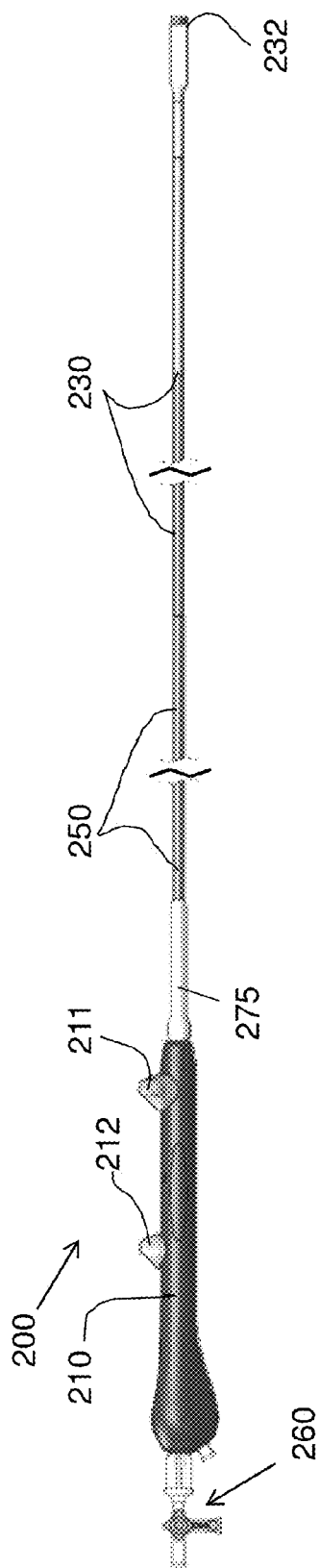
FIG. 2A is a plan view of a delivery system assembly, according to some embodiments.
Figure 2B:
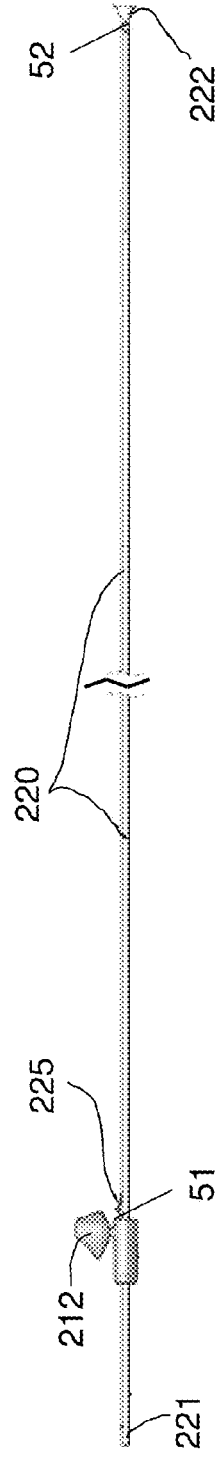
FIGS. 2B-C are plan views of inner and outer subassemblies, respectively, of the system assembly shown in FIG. 2A, according to some embodiments.
Figure 2C:
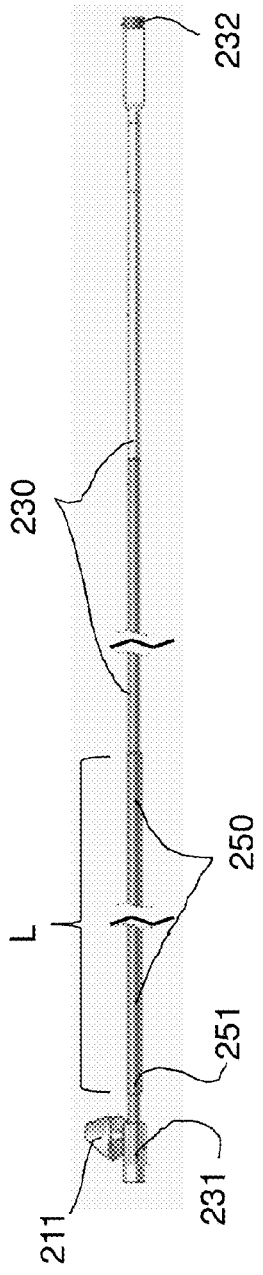

FIG. 2A is a plan view of a delivery system assembly 200, according to some embodiments. FIG. 2A illustrates system assembly including a handle 210 from which an elongate outer subassembly extends; the outer subassembly, which is also shown in FIG. 2C, includes an elongate outer tube 230 and a stability sheath 250 surrounding a length L of outer tube 230. With reference to FIGS. 2A and 2C, outer tube 230 is coupled to a first control member 211 of handle 210, for example, by a UV cure adhesive, and a proximal end 251 of stability sheath 250 is fixed to handle 210, distal to control member 211. FIG. 2B is a plan view of an inner subassembly that extends within the outer subassembly. FIG. 2B illustrates the inner subassembly including an elongate inner member 220, which extends from a proximal end 221 thereof to a flared distal end 222 thereof; proximal end 221 of inner member 220 is fixed within handle 210 and may be coupled to a luer fitting (not shown) to which a stop cock 260 is shown coupled in FIG. 2A. With reference to the cut-away section shown in FIG. 3A, flared distal end 222 is contained within a distal-most portion of outer tube 230, just proximal to a distal end 232 of outer tube 230, according to some embodiments. According to the illustrated embodiment, first control member 211 is slidable along handle 210 to move/retract outer tube 230 longitudinally, relative to inner member 220, from a first position 31, which is illustrated in FIG. 3A, to a second position 32, for example, where distal end 232 of outer tube 230 is approximately aligned with flared distal end 222 of inner member 220, which is illustrated in FIG. 3B. Alternately, second position 32 may be located more proximally, such that more of inner member is exposed distal to distal end 232 of outer tube 230, or more distally, such that only fixation member 115 of device 100 is exposed. According to some embodiments, an O-ring type seal member (i.e. silicone; not shown), which may be lubricated, for example, with silicone oil, forms a dynamic sealing interface between outer tube 230 and inner member 220 within handle 210, in proximity to first control member 211.

With further reference to FIG. 3A, device 100 is shown held within the distal-most portion of outer tube 230, just proximal to distal end 232. FIG. 3A further illustrates a proximal end 121 of device 100 abutting flared distal end 222 of inner member 220, which, preferably conforms to proximal end 121 of device 100. With reference back to FIG. 1B, it may be appreciated that delivery system assembly 200 is preferably employed in place of the illustrated guiding catheter 150, to deliver device 100 through the venous system and into proximity with a target implant site, for example, in the RV, when outer tube 230 is in first position 31 shown in FIG. 3A. According to an exemplary embodiment, a distal-most portion of outer tube 230, which contains device 100, has an inner diameter of approximately 0.275 inch (~0.7 cm) and an outer diameter of approximately 0.3 inch (~0.8 cm). Although FIG. 3A illustrates the distal-most portion of outer tube 230 being enlarged from a remainder of outer tube 230, for example, over a length of approximately 3.5 cm (~1.4 inch), according to alternate embodiments, an outer diameter along a more significant length up to an entire length of outer tube 230 may be the same as that of the distal-most portion. With reference to FIG. 3B, once delivery system assembly 200, with device 100 held therein, is positioned with distal end 232 of outer tube 230 adjacent to the target implant site, outer tube 230 is retracted, per arrow R (FIG. 3A), by means of first control member 211, to second position 32 (FIG. 3B), so that fixation member 115 of device 100 is exposed to secure electrode 111 to tissue at the implant site. According to FIG. 3B, almost an entirety of device 100 exposed when outer 230 is in second position 32; thus, a distance between first position 31 and second position 32 may be as small as approximately 2 cm up to approximately 6 cm, depending on the length of device 100. Alternately, second position 32, as mentioned above, may be located to only expose enough of fixation member 115 to secure device 100 at the implant site, in which case, the distance between the first and second positions may be as small as approximately 0.5 cm to 1 cm. According to some preferred embodiments, flared distal end 222 of inner member 220 is radiopaque and distal end 232 of outer tube 230 is fitted with a radiopaque marker, so that the retraction of outer tube 230, relative to flared distal end 222, for the deployment of device 100, can be observed via fluoroscopy. According to an exemplary embodiment, flared distal end 222 is formed from a polyether block amide, for example, PEBAX® 7033, with a radiopaque Barium sulfate filler; and the distal-most portion of outer tube 230 is formed from a polyether block amide, for example, PEBAX® 7233, which, at distal end 232, includes a radiopaque band of 75% Tungsten and 25% PEBAX® 6033 sandwiched between layers of the PEBAX® 7233.

Figure 4:
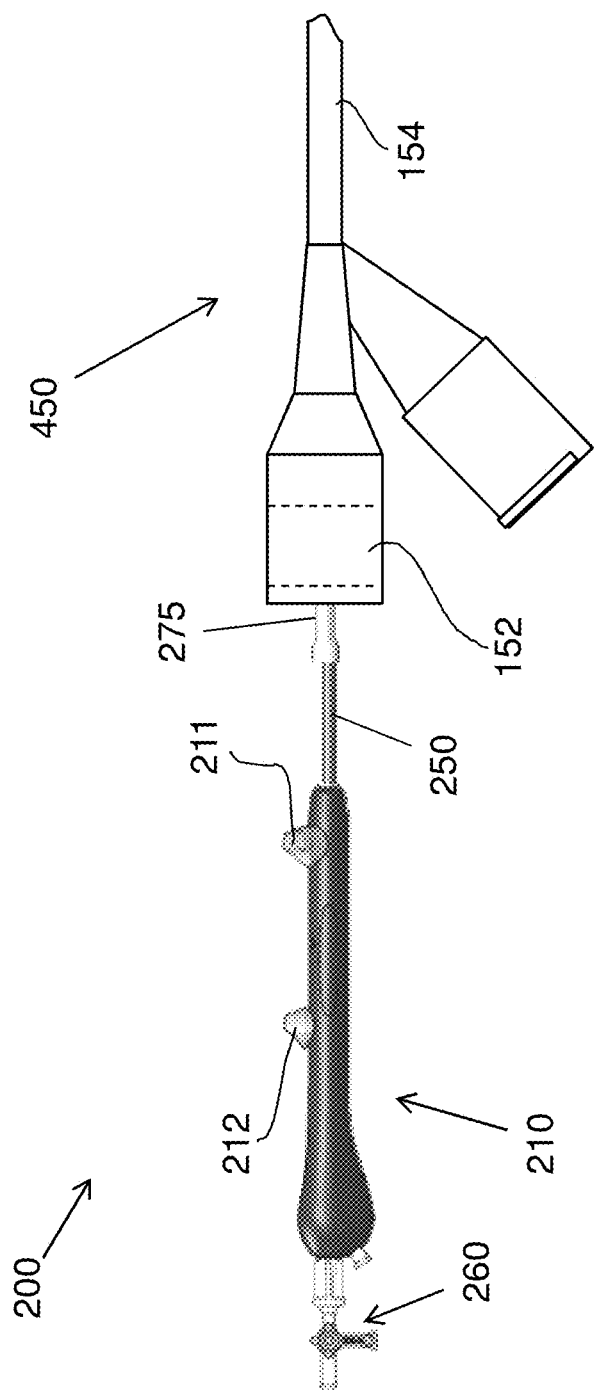
FIG. 4 is a plan view of the proximal portion of the delivery system assembly protruding from a proximal end of an introducer sheath.

According to embodiments of the present invention, stability sheath 250 is relatively rigid and allows for the above-described relative movement of outer tube 230 therein, so that, for example, an operator, who is handling delivery system assembly 200, cannot inadvertently, by applying a force around outer tube 230 in proximity to handle 210, impede the retraction of outer tube 230, during device deployment, which may cause inner member 220 to apply a push force against device 100 that may injure tissue at the implant site. With reference to FIG. 4, stability sheath 250 further prevents similar forces from being applied to outer tube 230 within an introducer sheath 450. Introducer sheath 450, such as the typical type known to those skilled in the art, provides percutaneous venous access for delivery system assembly 200 and has a relatively flexible shaft wall 154 that may collapse about system assembly 200 at the entry site into the venous system; furthermore, sheath 450 may include a valve 152 (designated with dashed lines) within a proximal hub thereof, which, to prevent blood backflow around the inserted system assembly 200, is compressed thereabout.

Stability sheath 250 preferably has an inner surface spaced apart from the outer tube by a radial gap, for example, being approximately 0.002 inch and approximately 0.01 inch; however, if the inner surface of stability sheath 250 is highly lubricious, the gap may be smaller. According to an exemplary embodiment, stability sheath 250 includes an inner polymer layer adhered to an outer polymer layer, for example, by a compatible extrudable tie-layer resin like PLEXAR®, wherein the inner polymer layer is formed from a high density polyethylene (HDPE), for lubricity, the outer layer is formed from a Nylon, for example, AESNO® Nylon 12, for relatively high radial strength; a wall thickness of each of the inner and outer layers is between approximately 0.005 inch (~0.13 mm) and approximately 0.025 inch (~0.65 mm), preferably approximately 0.012 inch. With reference back to FIG. 2C, length L of outer tube 230 which is surrounded by stability sheath 250 is preferably shorter than a length of introducer sheath 450, for example, between approximately 15 cm and approximately 53 cm, preferably between approximately 46 cm and approximately 53 cm, when an overall length of outer tube 203 between handle 210 and distal end 232, in first position 31, is approximately 103 to 107 cm. Thus, the relative rigidity of stability sheath 250 does not impact the flexibility of delivery system assembly 200, over that length which extends distally beyond introducer sheath 450, to hinder system maneuverability in advancing distal end 232 to the target implant site. With reference back to FIG. 2B, when introducer sheath 450 is between approximately 55 cm to 65 cm long, it may just reach into RA from a femoral venous access site.

With further reference to FIGS. 2A and 4, delivery system assembly 200 further includes an optional overlay 275, which is shown surrounding stability sheath 250, in proximity to handle 210. Optional overlay 275 provides an enhanced interface between system assembly 200 and valve 152 of introducer sheath 450, for example, for improved sealing and/or with additional radial strength to counteract a compressive force of valve 152, which, if valve 152 is a Tuohy Borst type, can be tightened down to different degrees depending upon the operator. Optional overlay 275 is preferably slidable over stability sheath 250 so that overlay 275 may be repositioned with respect to handle 210 in order to coincide with valve 152 of introducer sheath 450, following the introduction and advancement of system assembly 200 into proximity with the target implant site for deployment of device 100. Optional overlay 275, according to some embodiments, may also be temporarily positioned around outer tube 230, between a distal end of stability sheath 250 and the above-described enlarged distal-most portion of outer tube 230, to provide additional support as delivery system assembly 200 is being introduced into introducer sheath 450. According to an exemplary embodiment, optional valve interface overlay 275 is formed from a polyether block amide, for example, PEBAX® 7030, which may include a titanium oxide filler.

Figure 1A:
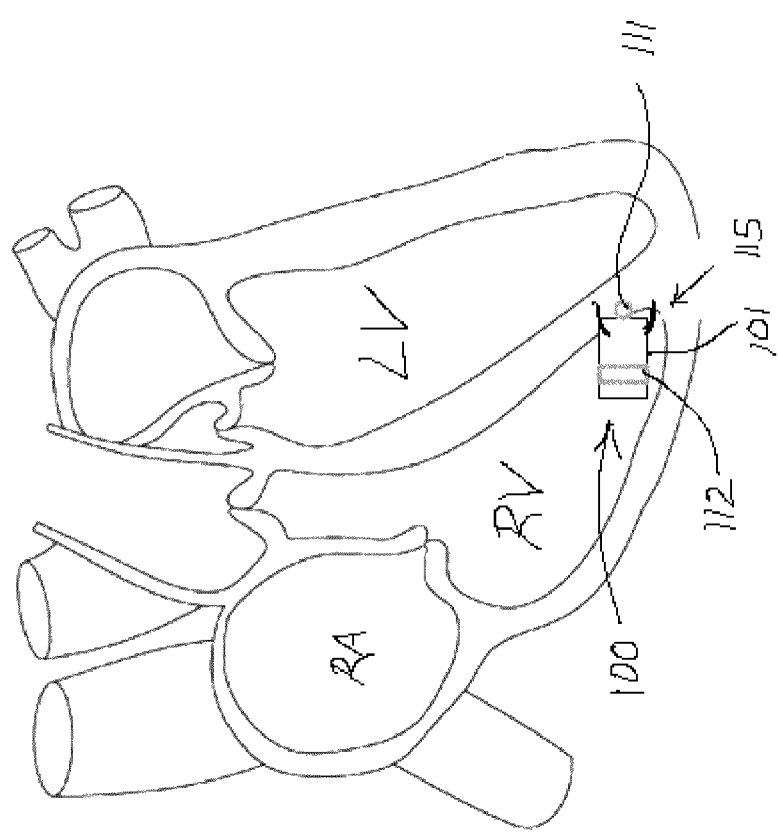
FIG. 1A is a schematic showing an example of an implanted cardiac stimulation device.
Figure 1B:
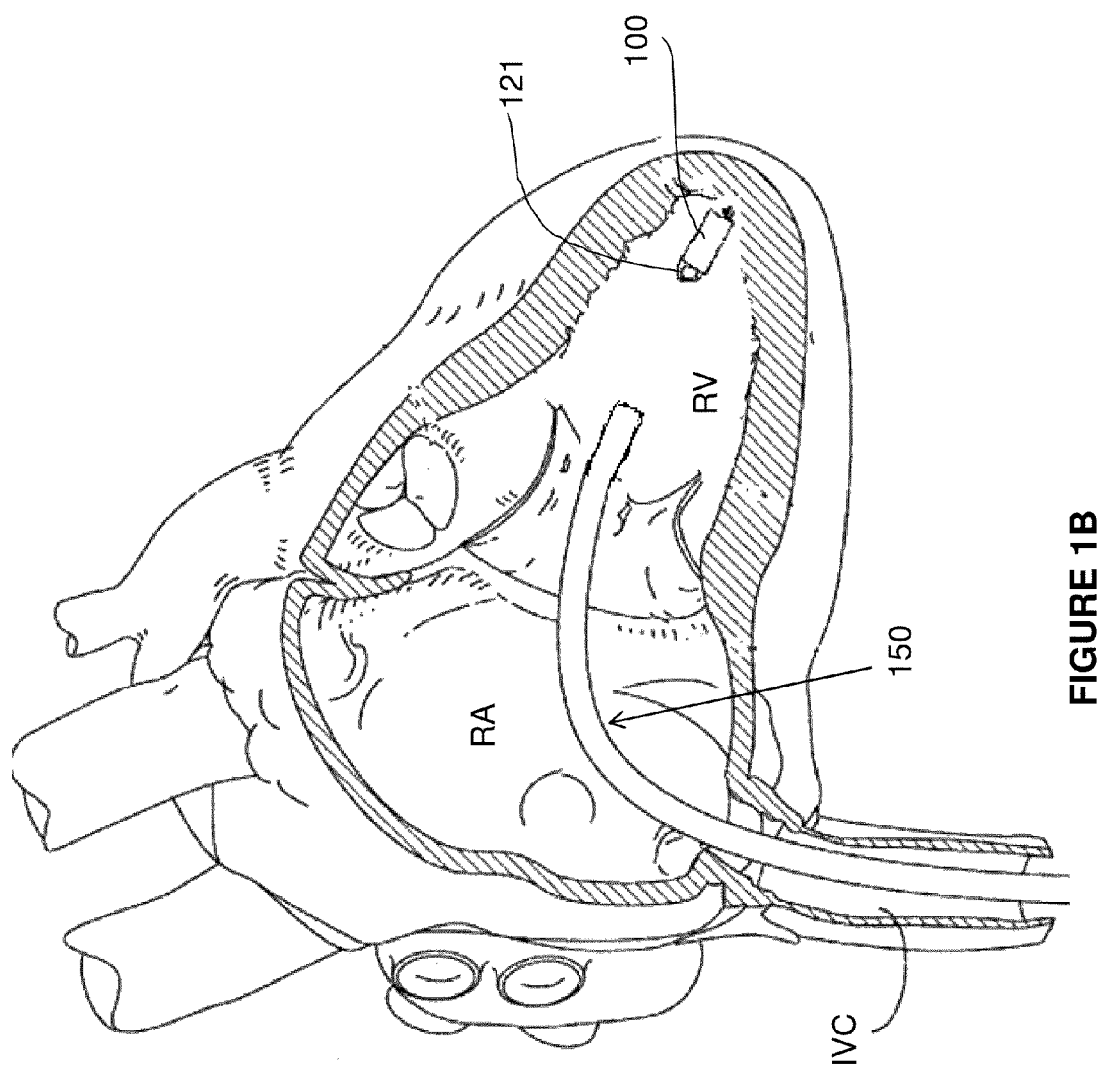
FIG. 1B is a schematic showing the implanted device along with a guiding catheter.
Figure 5:
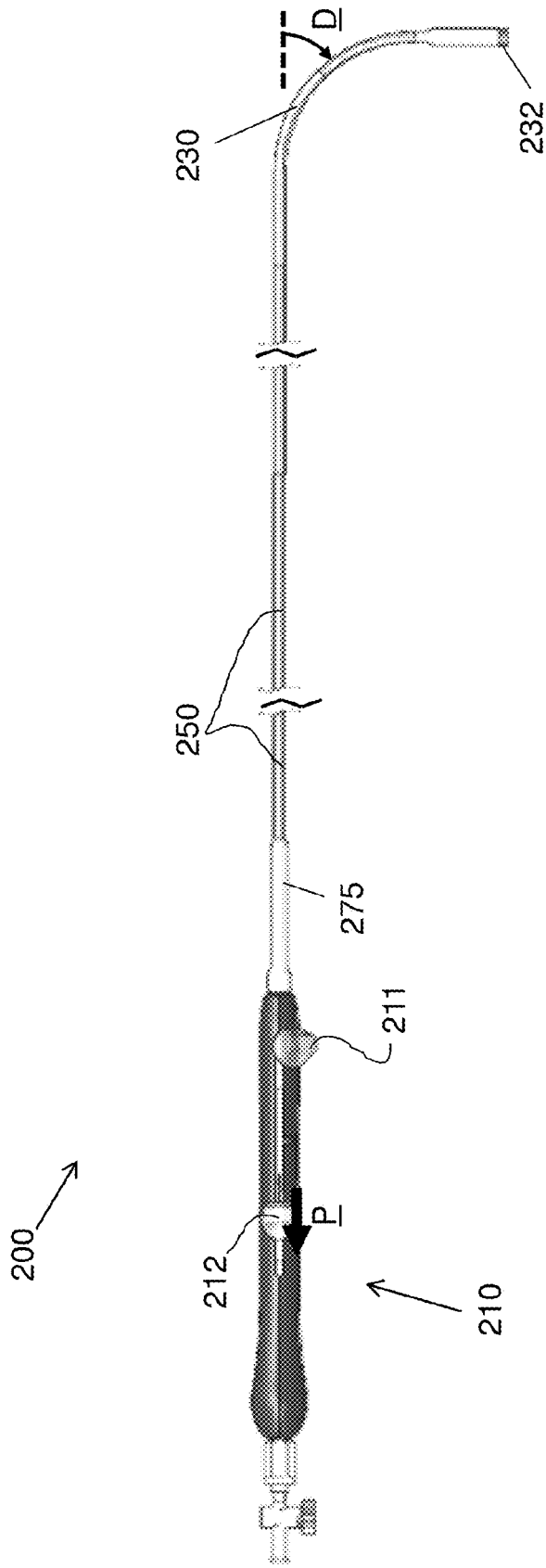
FIG. 5 is another plan view of the delivery system assembly, according to some embodiments.

FIG. 5 is another plan view of delivery system assembly 200, according to some embodiments, wherein a distal portion of outer tube 230 is shown deflected, per arrow D. Deflection of the distal portion of outer tube 230 may be useful in maneuvering delivery system assembly 200 to the target implant site, for example, into the RV through the tricuspid valve, from the RA, as shown in FIG. 1B. With reference back to FIG. 2B, according to some preferred embodiments, inner member 220 includes a pull wire 225, which extends along a length of inner member 220, preferably within a lumen (not shown) of inner member 220, to affect the deflection shown in FIG. 5. According to the illustrated embodiment, a proximal end 51 of pull wire 225 is coupled to a second control member 212 of handle 210 (FIG. 2A), and a distal end 52 of pull wire 225 is anchored in proximity to flared distal end 222 of inner member 220. A flexibility of a shaft that forms inner member 220, as well as that which forms outer tube 230, is preferably graduated from a relatively stiff proximal segment to a relatively flexible distal segment to facilitate the deflection illustrated in FIG. 5. With reference to FIG. 3A, when second control member 212 is moved, per arrow P, in a proximal direction, distal end 52 of pull wire 225 is pulled, per arrow P, to deflect the relatively flexible distal segment(s) of inner member, just proximal to flared distal end 222, and, thereby, cause deflection of the relatively flexible distal segment(s) of outer tube 230, for example, like that shown in FIG. 5. According to the illustrated embodiment, a shoulder 233 is formed at the transition from a lumen LD of the enlarged distal-most portion, which contains device 100, to a smaller diameter lumen LP that extends proximally within tube 230, such that flared distal end 222 may seat against shoulder 233 to enhance the deflection, in some instances.

The construction of shafts for inner member 220 and outer tube 230 may be any suitable type known in the art to achieve suitable graduated flexibility for the necessary maneuverability thereof, which includes pushability and torque transfer, as well as the above described deflection. According to an exemplary embodiment, the shaft of inner member 220 extends over a length of approximately 118 cm, from proximal end 221 to the site where distal end 52 of pull wire 225 is anchored, just proximal to flared distal end 222, and includes a stainless steel braid (0.0012"×0.003"×70 PPI) surrounding a PEBAX® 7033 liner, a proximal layer of Trogamid® polyamide overlaying the braid, along a length of approximately 108 cm, and a distal layer of Vestamid® polyamide overlaying the braid, along a length of approximately 10 cm; a proximal segment of the shaft is further overlaid with AESNO® Nylon 12 along a length of approximately 100 cm; an intermediary segment of the shaft, which extends distally from the proximal segment over a length of approximately 11 cm, is further overlaid with PEBAX® 55; and a distal segment of the shaft, which extends distally from the intermediary segment to the site where pull wire 225 is anchored, over a length of approximately 7 cm, is further overlaid with PEBAX® 3533. Furthermore, according to the exemplary embodiment, outer tube 230 includes a braid reinforced liner, for example, PEBAX® 6333 with a stainless steel braid (i.e. 0.0018"×0.008"×45 PPI) extending from proximal end 231 to just proximal to the above-described enlarged distal-most portion of outer tube 230; a proximal segment of the shaft is overlaid with PEBAX® 7033 and extends over a length of approximately 92 cm (a proximal portion of which length is always contained within handle 210); an intermediary segment of the shaft is overlaid with PEBAX®4033 and extends distally from the proximal segment over a length of approximately 10 cm; and a distal segment of the shaft is overlaid with PEBAX® 3533 and extends distally from the intermediary segment, over a length of approximately 3 cm, to just proximal to the distal-most portion. Outer and inner diameters of outer tube 230, along the above-described segments, may be approximately 0.187 inch (~4.75 mm) and approximately 0.154 inch (~3.91 mm), respectively.

The shaft of inner member 220, according to some preferred embodiments, has an outer diameter of approximately 0.112 inch (~2.85 mm) and includes a pair of lumens; a first of the lumens has a diameter of approximately 0.015 inch (~0.38 mm), and a second of the lumens has a diameter of approximately 0.077 inch (~1.96 mm). The first lumen accommodates pull wire 225, while the second lumen may accommodate a tether, which is initially attached to device 100 during the implant procedure. As system 200 is advanced and maneuvered into position in proximity to the target implant site, the tether may be means by which device 100 is retained within the distal-most portion of outer tube 230 with proximal end 121 abutting flared distal end 222 of inner member 220; alternately, flared distal end 222 may be configured to retain device 100 until outer tube 230 is retracted for the deployment of device 100. (After device 100 is deployed, the tether is useful for pulling device 100 back into distal end 232 of outer tube 230, if device 100 needs to be repositioned at an alternative site, otherwise the tether is detached from device 100 and pulled proximally within the second lumen of inner member 220.)

In the foregoing detailed description, the invention has been described with reference to specific embodiments. However, it may be appreciated that various modifications and changes can be made without departing from the scope of the invention as set forth in the appended claims.

We claim:

1. A delivery system assembly facilitating deployment of an implantable medical device, the assembly comprising:
a handle including at least one control member; an elongate inner member including a proximal end fixed within the handle, and a flared distal end spaced distally apart from the handle and configured to conform to a proximal end of the implantable medical device, wherein the elongate inner member includes a pull wire extending from a proximal end thereof, contained within the handle, to a distal end thereof anchored to the inner member in proximity to the flared distal end of the inner member;
an elongate outer tube forming a lumen in which the inner member extends, the outer tube including a proximal end and a distal end, the proximal end of the outer tube being contained within the handle and coupled to one of the at least one control member of the handle, the lumen of the outer tube being sized to hold the medical device in proximity to the distal end of the outer tube, and to allow retraction of the outer tube relative to the inner member, from a first position to a second position, the retraction of the outer tube being controlled by the control member to which the proximal end of the outer tube is coupled, and the first position corresponding to the distal end of the outer tube being spaced distally from the flared distal end of the inner member so that an entirety of the medical device can be contained within the lumen of the outer tube between the distal end thereof and the flared distal end of the inner member at the first position; and
a stability sheath surrounding a length of the outer tube and including a proximal end fixed to the handle, the stability sheath being relatively rigid and allowing movement of the outer tube relative thereto, for retraction;
wherein the length of the outer tube surrounded by the stability sheath is less than a distance between the handle and the distal end of the outer tube, when the outer tube is in either the first position or the second position.

2. The assembly of claim 1, wherein the length of the outer tube surrounded by the stability sheath is between approximately 15 cm and approximately 53 cm.

3. The assembly of claim 2, wherein the distance between the handle and the distal end of the outer tube, when the outer tube is in the first position, is between approximately 103 cm and approximately 107 cm.

4. The assembly of claim 1, wherein the stability sheath comprises an inner polymer layer adhered to an outer polymer layer by a compatible extrudable tie-layer resin.

5. The assembly of claim 4, wherein the inner polymer layer of the stability sheath comprises a relatively lubricious polymer.

6. The assembly of claim 1, wherein an inner surface of the stability sheath is spaced apart from the outer tube by a radial gap between approximately 0.002 inch and approximately 0.01 inch.

7. The assembly of claim 1, further comprising a valve interface overlay surrounding the stability sheath in proximity to the handle, the overlay being slidable over the stability sheath for repositioning of the overlay with respect to the handle.

8. The assembly of claim 1, wherein, when the outer tube is in the first position and the proximal end of the medical device abuts the flared distal end, an entirety of the medical device is contained within the outer tube, in proximity to the distal end thereof.

9. The assembly of claim 1, wherein the second position corresponds to the distal end of the outer tube being approximately aligned with the flared distal end of the inner member.

10. The assembly of claim 1, wherein a distance between the first position and the second position ranges from approximately 2 cm to approximately 6 cm.

11. The assembly of claim 1, wherein the flared distal end of the inner member is radiopaque.

12. The assembly of claim 1, wherein a distal portion of the lumen of the outer tube between the distal end of the outer tube and the flared distal end of the inner member has a length corresponding to the length of the entirety of the medical device.

13. The assembly of claim 1, wherein in the first position, the distal end of the outer tube and the flared distal end of the inner member are spaced apart by a first length that corresponds to a length of the entirety of the medical device.

* * * * *